United States Patent [19]

Baglioni

[11] Patent Number: 4,568,690
[45] Date of Patent: Feb. 4, 1986

[54] 1-METHYL-5-P-METHYLBENZOYLPYR-ROLE-2-ACETAMIDOACETANILIDES WITH ANTIINFLAMMATORY, ANALGESIC, ANTIPYRETIC AND ANTI-PLATELET AGGREGANT ACTIVITY

[75] Inventor: Alessandro Baglioni, Rome, Italy

[73] Assignee: Medosan Industrie Biochimide Riunite S.P.A., Albano Laziale, Italy

[21] Appl. No.: 634,490

[22] Filed: Jul. 26, 1984

[30] Foreign Application Priority Data

Jul. 29, 1983 [IT] Italy ................. 48781 A/83

[51] Int. Cl.$^4$ .................................... C07D 207/323
[52] U.S. Cl. .................................... 514/423; 548/539
[58] Field of Search ................... 548/539; 514/423

[56] References Cited

U.S. PATENT DOCUMENTS

| | | | |
|---|---|---|---|
| 3,952,012 | 4/1976 | Carson | 548/539 X |
| 4,070,368 | 1/1978 | Carson | 548/539 X |
| 4,200,645 | 4/1980 | Goudie | 548/539 X |
| 4,379,793 | 4/1983 | Badia | 514/423 |
| 4,396,626 | 8/1983 | Ward et al. | 514/423 |
| 4,434,175 | 2/1984 | Doherty et al. | 514/423 |
| 4,521,538 | 6/1985 | Baglioni | 548/539 X |

FOREIGN PATENT DOCUMENTS

| | | | |
|---|---|---|---|
| 0051981 | 5/1982 | European Pat. Off. | 548/539 |
| 0088734 | 9/1983 | European Pat. Off. | 548/539 |
| 3306006 | 9/1983 | Fed. Rep. of Germany | 548/539 |
| 55-24141 | 2/1980 | Japan | 548/539 |
| 2098989 | 12/1982 | United Kingdom | 548/539 |
| 2115417 | 9/1983 | United Kingdom | 548/539 |
| 2134111 | 8/1984 | United Kingdom | 548/539 |

OTHER PUBLICATIONS

Abstract of Japan Application 0144256; Sep. 6, 1982.

Primary Examiner—Joseph Paul Brust
Attorney, Agent, or Firm—Cushman, Darby & Cushman

[57] ABSTRACT

The anilide derivates of 1-methyl-5-p-methylbenzoyl-pyrrole-2-acetamidoacetic acid are described, with general formula

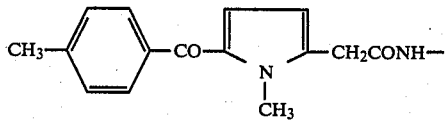

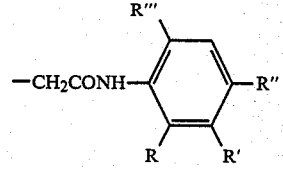

in which R, R', R" and R'" may be hydrogen, halogen, alkyl, alkoxyl or a trifluoromethyl group. The compounds show useful antiinflammatory analgesic, antipyretic and antiplatelet aggregant activities.

11 Claims, No Drawings

1-METHYL-5-P-METHYLBENZOYLPYRROLE-2-ACETAMIDOACETANILIDES WITH ANTIINFLAMMATORY, ANALGESIC, ANTIPYRETIC AND ANTI-PLATELET AGGREGANT ACTIVITY

BACKGROUND OF THE INVENTION

1. Field of the Invention

The present invention concerns substituted anilide derivatives of 1-methyl-5-p-methylbenzoylpyrrole-2-acetamidoacetic acid, prepared by amidation of said acid with suitably substituted anilines. These anilides are endowed with therapeutically useful antinflammatory, analgesic, antipyretic and anti-platelet aggregant activity.

They are represented by general formula (1)

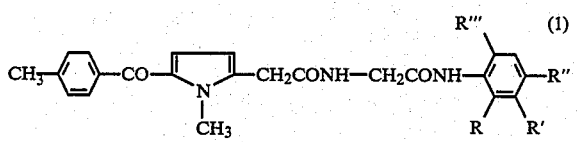

in which R, R', R", R''' may be:
(a) a hydrogen
(b) a halogen, respectively chlorine, bromine and fluorine, but preferably chlorine and fluorine
(c) a straight or branched alkyl chain, respectively methyl, ethyl, . . . , but preferably a methyl group
(d) an alkoxyl group, respectively methoxyl, ethoxyl, . . . , but preferably methoxyl
(e) a trifluoromethyl group.

2. Description of the Prior Art

All these compounds are structural derivatives of 1-methyl-5-p-methylbenzoylpyrrole-2-acetamidoacetic acid (2)

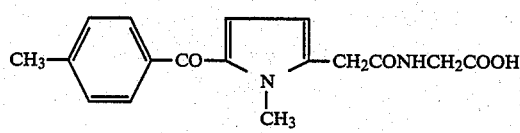

the antinflammatory properties of which were the object of a previous patent of Medosan S.p.A. (Italian application n. 47881 A/82 of Feb. 26, 1982 corresponding to U.S. application Ser. No. 467,308, field Feb. 17, 1983 and now abandoned), which is in turn derived from 1-methyl-5-p-methylbenzoylpyrrole-2-acetamidoacetic acid (3)

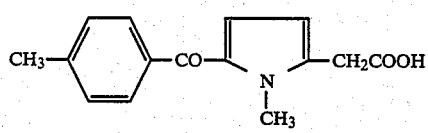

(U.S. patent application Ser. No. 656,074 of July 26, 1967, now abandoned, in the name of J. R. Carson), a known antinflammatory agent known by the generic name of Tolmetin and used in therapy as the dihydrate sodium salt.

The anilides with formula (1) are examples of isosteric derivatives of the 1-methyl-5-p-methylbenzoylpyrrole-2-acetamidoacetate of o-methoxyphenol (4), an ester with antinflammatory, analgesic, antipyretic, antisecretive and cough suppressing activity greater than that of Tolmetin, with longer lasting action and lower toxicity.

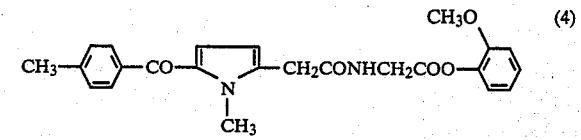

SUMMARY OF THE INVENTION

The anilides of formula (1) according to the present invention not only possess antinflammatory, analgesic and antipyretic activity, but also show anti-platelet aggregant activity, which was not predicted on the basis of the prior art. In particular, derivative 1d (R=OCH$_3$, R'=R"=R'''=H), in addition to showing said activities to a degree comparable to that of the ester analogue (4), also shows a particularly pronounced anti-platelet aggregant activity.

Anilides (1) also show low toxic effects at the level of the gastroenteric tract, unlike Tolmetin (3), acid (2) and acid antinflammatories in general, since they have no free carboxyl function, as the latter is blocked as an amide. Said anilides thus belong to the non-steroid, non-acid class of antinflammatory agents, with considerably reduced or almost nil ulcerogenic effect.

Therefore the object of the present invention are new amide structure antinflammatory agents of a non-acid nature, derivatives of 1-methyl-5-p-methylbenzoylpyrrole-2-acetamidoacetic acid (2) in combination with suitably substituted anilines, which not only present higher antinflammatory activity than that of Tolmetin and are longer lasting in effect, but also show pronounced anti-platelet aggregant activity. These activities, plus the analgesic and antipyretic action, are useful from a therapeutic point of view.

DESCRIPTION OF THE PREFERRED EMBODIMENTS

Preparation of the compounds according to the invention

The general process for the preparation of compounds of formula (1) comprises the operation of reacting at a temperature between 60° and 80° C., in the presence of aprotic or protic solvents as a function of the activating group, a substituted aniline of general formula

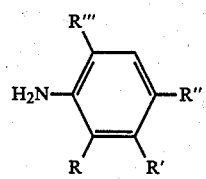

in which R, R', R" and R''' have the same meaning as above, with an activated derivative of 1-methyl-5-p-methylbenzoylpyrrole-2-acetamidoacetic acid of general formula

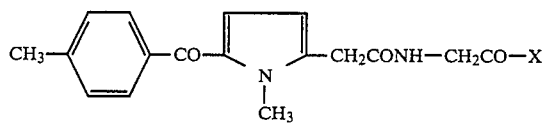

in which X is an activating group which can promote an amide bond with the previously indicated amines, selected from the class comprising the

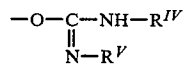

residue, in which $R^{IV}$ and $R^V$ are alkyl groups with 1 to 3 carbon atoms or cycloalkyl groups with 5 to 6 carbon atoms, and the residue

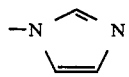

The amount of amine used varies from 1 to 1.5 times the equivalent amount of acid (2), preferably 1.2 equivalents. The condensing agent may be N,N'-dicyclohexylcarbodiimide or a mixture of it with p-toluenesulfonic acid or 4-dimethylaminopyridine in catalytic quantities, or alternatively N,N'-carbonyldiimidazole in the presence or absence of ethyl magnesium. Other dehydrating agents or the action of the acid chloride of (2) or its mixed anhydride on the anilines reported in Table I give anilides (1) in an analogous fashion.

TABLE I

Substituted anilines used as reagents in the condensation with 1-methyl-5-p-methyl-benzoylpyrrole-2-acetamidoacetic acid

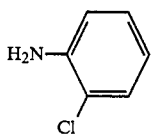 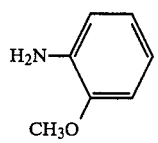

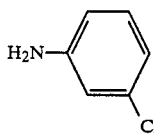 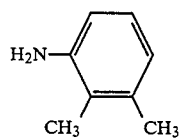

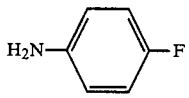 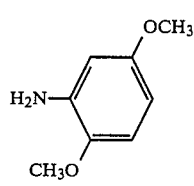

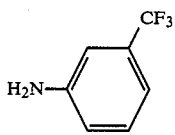

The reaction is schematically illustrated by the condensation of acid (2) and o-chloroaniline.

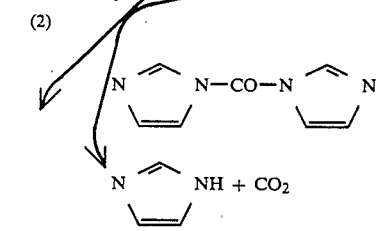

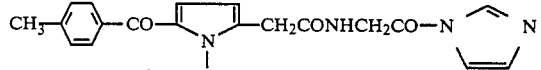

(1a)

The reaction is generally carried out in non-polar medium, although water-dioxane and water-tetrahydrofuran mixtures are used occasionally, using N,N'-dicyclohexylcarbodiimide with or without catalyst as condensing agent. The solvents used most often are dichloromethane, dichloroethane, tetrahydrofuran, dioxane, dimethylsulfoxide, N,N'-dimethylformamide. The best yields are obtained with anhydrous solvents, and range from 18 to 85%, with an average of about 60%. The reaction temperature is in the range 60° to 80° C. The reaction must be carried out with strong stirring, under nitrogen or other inert gas where necessary, by means of gradual addition of the reagents. The reaction mixtures are worked up in the usual way, using common separation techniques such as filtration, centrifugation or adsorption on a suitable inert material where necessary for purification. The latter is generally performed by means of crystallization from a suitable solvent to give all the amides (1) described in the form of crystalline solids.

A detailed description of the preparation of the anilides (1) is reported as an example which may be generalized to all the anilines reported in Table I.

The identity of the anilides (1) was confirmed by analysis of the IR spectra, and when necessary NMR and mass spectra. All the compounds (1) were submitted to elemental analysis, and the analytical data found were in the range ±0.3% of the theoretical values calculated.

The compounds which form the object of the present invention are reported in Table II, and their preparation is illustrated by the following general example.

GENERAL METHOD FOR THE PREPARATION OF ANILIDES OF FORMULA (1)

A solution of 1-methyl-5-p-methylbenzoylpyrrole-2-acetamidoacetic acid (2) (3.14 g, 10 mmol) in 100 ml of anhydrous tetrahydrofuran (THF) is treated with a solution of N,N'-carbonylidimidazole (CDI) (1.94 g, 12 mmol) in 100 ml of anhydrous THF. During the addition a precipitate forms consisting of the imidazolide of the acid with formula (2). After the addition, the mixture is stirred at room temperature for one hour, and then treated with a solution of the appropriate aromatic amine (12 mmol) dissolved in 50 ml of anhydrous THF. The resulting suspension is first stirred energetically at room temperature for 2 hours, and then heated at reflux for 2 more hours. A clear solution is obtained. The solvent is removed under vacuum over a hot oil bath, and the oily or solid residue obtained is dissolved in ethyl acetate (300 ml). The organic solution is washed first with 1N NaOH (2×50 ml) to remove the unreacted acid starting material, then with 1N HCl (2×50 ml) to remove any unreacted amine and finally with water (3×100 ml) until neutral. After drying over anhydrous sodium sulfate, the solution is filtered and the solvent is removed under vacuum over a hot oil bath. The solid so obtained is crystallized from a suitable solvent (see Table II).

caused no significant toxic effects. Optimal gastric tolerance was also shown.

As an example, the experimental data were reported here for the activity of the test compound administered, in comparison with the dihydrate sodium salt of 1-methyl-5-p-tolylpyrrole-2-acetic (tolmetin-2H$_2$O), known in the literature for its antinflammatory, analgesic and antipyretic activity (S. Wong, J. F. Gardocki, and T. P. Pruss, *J. Pharmac. Exp. Ther.*, 185 (1), 127 (1973)). The anti-platelet aggregant activity was compared with that of aspirin.

ANTINFLAMMATORY ACTIVITY

This effect was evaluated with an experimental model reproducing actue inflammation in rats: the carragenin-induced edema test was used, according to the method of C. A. Winter (*G. Pharmac. Exp. Ther.*, 141, 369 (1963)). Table III reports the compounds tested, their concentrations, administration routes and relative percent edema inhibition.

TABLE II

Anilides of 1-methyl-5-p-methylbenzoyl-pyrrole-2-acetamidoacetic acid.

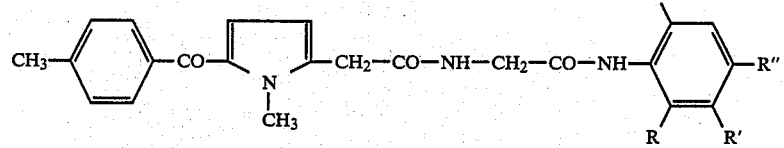

| Compound | R | R' | R'' | R''' | Formula | Molecular weight | Melting point °C. | Yield % | Crystallized from |
|---|---|---|---|---|---|---|---|---|---|
| 1 a | Cl | H | H | H | C$_{23}$H$_{22}$ClN$_3$O$_3$ | 423.94 | 183–185 | 18.8 | ethanol |
| 1 b | H | Cl | H | H | C$_{23}$H$_{22}$ClN$_3$O$_3$ | 423.94 | 194–195 | 44.8 | ethanol |
| 1 c | H | H | F | H | C$_{23}$H$_{22}$FN$_3$O$_3$ | 407.48 | 208–210 | 65.0 | ethanol |
| 1 d | OCH$_3$ | H | H | H | C$_{24}$H$_{25}$N$_3$O$_4$ | 419.46 | 153–155 | 85.0 | ethanol |
| 1 e | H | CF$_3$ | H | H | C$_{24}$H$_{22}$F$_3$N$_3$O$_4$ | 457.44 | 173–175 | 61.2 | ethanol |
| 1 f | CH$_3$ | CH$_3$ | H | H | C$_{25}$H$_{27}$N$_3$O$_3$ | 417.49 | 215–219 | 24.4 | N,N—dimethylformamide |
| 1 g | H | OCH$_3$ | H | OCH$_3$ | C$_{25}$H$_{27}$N$_3$O$_5$ | 449.49 | 184–186 | 44.5 | ethanol-ethyl acetate (1:1) |

PHARMACOLOGICAL PROPERTIES

The experiments carried out with compounds 1b, 1d, 1f, 1g (anilides of 1-methyl-5-p-methylbenzoylpyrrole-2-acetamidoacetic acid) and reported in Table II show these compounds have pharmacological properties therapeutically useful in certain pathological conditions. Preparations of the compound were administered orally and/or parenterally in a suspension in 0.59% carboxymethylcellulose in pH neutral physiological saline.

In particular, the test compounds showed inhibitory action on acute inflammation, together with pronounced peripheral analgesic action. It was also shown, as reported below, that these derivatives have good antipyretic activity and a pronounced anti-platelet aggregant effect. These pharmacotherapeutic effects were obtained using dosages and administration routes that

TABLE III

Antinflammatory activity of 1-methyl-5-p-methylbenzoylpyrrole-2-acetamido-acetanilides - compounds 1b, 1d, 1f, 1g.

| Compound | Dose mg/kg | Oedema inhibition % os 3 h | 6 h | 24 h | i.p. 3 h | 6 h | 24 h |
|---|---|---|---|---|---|---|---|
| Carrier | — | 0.0 | 0.0 | 0.0 | 0.0 | 0.0 | 0.0 |
| Tolmetin Na.2H$_2$O | 10 | 32.0 | 20.0 | 0.0 | 33.7 | 30.1 | 0.0 |
| Tolmetin Na.2H$_2$O | 50 | 46.8 | 45.0 | 0.0 | 47.1 | 44.0 | 0.0 |
| Tolmetin Na.2H$_2$O | 100 | 56.1 | 54.3 | 8.9 | 58.3 | 52.2 | 5.3 |
| 1b | 10 | 29.8 | 22.3 | 0.0 | 30.1 | 29.0 | 0.0 |
| " | 50 | 47.3 | 44.1 | 0.0 | 49.2 | 43.5 | 2.3 |
| " | 100 | 61.9 | 59.8 | 15.3 | 65.4 | 62.0 | 16.4 |
| 1d | 10 | 47.2 | 40.0 | 9.0 | 48.7 | 36.5 | 0.0 |
| " | 50 | 58.5 | 54.0 | 30.0 | 59.2 | 52.0 | 18.9 |
| " | 100 | 77.1 | 66.0 | 38.0 | 78.6 | 66.3 | 30.5 |
| 1f | 10 | 32.6 | 34.1 | 0.0 | 37.1 | 33.4 | 0.0 |
| " | 50 | 49.1 | 49.0 | 3.4 | 51.6 | 53.9 | 4.2 |
| " | 100 | 69.7 | 69.0 | 22.1 | 72.5 | 70.0 | 19.1 |
| 1g | 10 | 30.4 | 37.9 | 1.2 | 35.6 | 37.0 | 0.0 |
| " | 50 | 51.4 | 49.0 | 7.9 | 50.1 | 50.0 | 6.1 |
| " | 100 | 72.3 | 70.0 | 25.1 | 71.0 | 71.5 | 22.9 |

ANALGESIC ACTIVITY

The analgesic activity of compounds 1b, 1d, 1f, 1g was evaluated using the p-phenylquinone-induced writhing test, according to the method of E. Siegmund (Proc. Soc. Exp. Med. 95, 729 (1957)). The determination was made an hour after administration of the product. The inhibitory effect on abdominal contractions induced by phenyl-p-quinone was calculated as follows:

% protection =

$$\frac{\text{No. contractions (controls)} - \text{No. contractions (treated)}}{\text{No. contractions (controls)}} \times 100$$

Table IV reports the doses, the administration routes and their effectiveness expressed as % protection.

TABLE IV

Analgesic activity of 1-methyl-5-p-methylbenzoylpyrrole-2-acetamidon-acetanilides - compounds 1b, 1d, 1f, 1g.

| Compound | Dose mg/kg | Protection % os | i.p. |
|---|---|---|---|
| Carrier | — | 0.0 | 0.0 |
| Tolmetin Na.2H$_2$O | 5 | 15.0 | 16.5 |
| " | 10 | 40.6 | 46.2 |
| " | 20 | 62.0 | 69.3 |
| 1b | 5 | 16.1 | 18.7 |
| " | 10 | 36.2 | 42.3 |
| " | 20 | 69.1 | 69.5 |
| 1d | 5 | 22.9 | 29.0 |
| " | 10 | 54.2 | 60.1 |
| " | 20 | 70.1 | 73.4 |
| 1f | 5 | 18.0 | 15.3 |
| " | 10 | 42.1 | 47.0 |
| " | 20 | 70.3 | 75.0 |
| 1g | 5 | 20.1 | 23.0 |
| " | 10 | 50.3 | 56.9 |
| " | 20 | 76.0 | 74.2 |

ANTIPYRETIC ACTIVITY

This effect was evaluated by inducing hyperthermia in Wistar strain male albino rats with an average weight of 250±10 g, injecting them intraperitoneally with a 10% suspension of dry purified beer yeast (Carlo Erba) in a volume of 10 ml/Kg of body weight, according to the method of S. Wong et al. (J. Pharmac. Exp. Ther., 185 (1), 127 (1973)). The data are reported in Table V.

TABLE V

Antipyretic activity of 1-methyl-5-p-methylbenzoylpyrrole-2-acetamidoacet-anilides - compounds 1b, 1d, 1f, 1g.

| Compound | Dose mg/kg | Temperature decrease % os | | | i.p. | | |
|---|---|---|---|---|---|---|---|
| | | 1 h | 6 h | 24 h | 1 h | 2 h | 3 h |
| Carrier | — | 0.0 | 0.0 | 0.0 | 0.0 | 0.0 | 0.0 |
| Tolmetin Na.2H$_2$O | 50 | 18.0 | 20.0 | 29.5 | 16.0 | 19.0 | 31.0 |
| Tolmetin Na.2H$_2$O | 75 | 20.0 | 26.0 | 27.0 | 20.0 | 29.2 | 34.7 |
| Tolmetin Na.2H$_2$O | 100 | 32.0 | 30.9 | 47.2 | 28.0 | 39.1 | 31.3 |
| 1b | 50 | 19.0 | 19.5 | 29.8 | 16.0 | 19.3 | 33.0 |
| " | 75 | 20.0 | 30.0 | 40.1 | 26.0 | 36.1 | 40.0 |
| " | 100 | 30.0 | 33.1 | 31.2 | 39.1 | 40.0 | 30.5 |
| 1d | 50 | 16.0 | 22.0 | 30.1 | 18.0 | 26.0 | 39.0 |
| " | 75 | 18.0 | 28.0 | 48.2 | 30.0 | 36.1 | 56.1 |
| " | 100 | 29.0 | 32.0 | 50.0 | 42.0 | 49.0 | 48.0 |
| 1f | 50 | 15.1 | 20.0 | 28.7 | 12.1 | 25.0 | 29.8 |
| " | 75 | 18.2 | 29.5 | 28.7 | 16.3 | 30.1 | 35.1 |
| " | 100 | 22.1 | 32.0 | 38.1 | 38.7 | 43.0 | 40.0 |
| 1g | 50 | 17.1 | 27.1 | 29.1 | 26.0 | 27.0 | 26.0 |
| " | 75 | 19.6 | 30.1 | 43.1 | 32.1 | 34.5 | 40.0 |
| " | 100 | 23.1 | 33.0 | 42.1 | 39.1 | 46.0 | 41.0 |

ANTI-PLATELET AGGREGANT ACTIVITY

This activity was studied in vitro following Born's method (G. W. R. Born, Nature, 194, 937 (1962)) and inducing platelet aggregation with ADP. Platelet rich plasma was prepared by centrifuging 9 parts rat blood with 1 part 3.13% trisodium citrate solution, for 10 minutes at 2000 rpm. For the aggregation test, 0.2 ml of platelet rich plasma was mixed with a NaCl solution (0.9%) to which the test substance was added up to a final volume of 0.6 ml. Incubation was fixed at 3 minutes at 27° C. After aggregation was induced with ADP, the course of the aggregation was monitored continuously with an Elvi 840 Aggregometer (Elvi Logos—Milan). The antiaggregant effects were determined by the difference in the light transmission of the sample with respect to that of the ADP control. The test compound was compared with aspirin, which has known antiplatelet aggregant activity (H. J. Weiss et al., J. Clin. Inv., 47, 2169 (1968); Platelet Aggregation and Drugs, edited by L. Caprino and E. C. Rossi, page 235, Academic Press (London), 1974).

Table VI reports the inhibition of platelet aggregation with various doses of the compounds tested at a constant ADP concentration.

TABLE VI

"In vitro" anti platelet aggregant activity of 1-methyl-5-p-methylbenzoylpyrrole-2-acetamidoacetanilides: compounds 1b, 1d, 1f at constant ADP concentration

| Inducer | Compound | Dose | Inhibition % |
|---|---|---|---|
| ADP 7.08 μmol/l | 1b | 1 γ/ml | 25 |
| " | " | 5 γ/ml | 100 |
| " | " | 10 γ/ml | 100 |
| " | 1d | 1 γ/ml | 20 |
| " | " | 5 γ/ml | 70 |
| " | " | 10 γ/ml | 90 |
| " | 1f | 1 γ/ml | 22 |
| " | " | 5 γ/ml | 75 |
| " | " | 10 γ/ml | 90 |
| " | Aspirin | 1 γ/ml | 15 |
| " | " | 5 γ/ml | 60 |
| " | " | 10 γ/ml | 100 |

GASTRIC TOLERANCE

This was studied by testing ulcerogenic activity in male Wistar rats weighing an average of 180 g, using groups of 10 animals each. Three doses of each substance were used, and one group of animals was treated with vehicle only, in a volume of 10 ml/g body weight. Each dose was administered orally for four consecutive days, and the rats were killed on the fifth day and autopsied. The ulcerogenic effect was evaluated on the following scale:

NUMBER OF LESION (1) each hemorrhage point >1 mm was evaluated as 1 lesion
(2) the hemorrhage points <1 were counted as follows:

| | |
|---|---|
| (a) from 1 to 9 | 1 lesion |
| (b) from 1 to 19 | 2 lesions |
| (c) from 1 to 29 | 3 lesions |

SEVERITY OF LESION

| | |
|---|---|
| (1) no lesions | 0 |
| (2) gastric mucosa irritation | 1 |
| (3) hemorrhage points <1 mm | 2 |
| (4) hemorrhage points from 1 to 3 mm | 3 |
| (5) hemorrhage points >3 mm | 4 |
| (6) perforations | 5 |

This scale was used to calculate the following index of gastric damage:

$$I = \text{mean No. lesions} + \text{mean severity} + \frac{\text{incidence \%}}{10}$$

The data are reported in Table VII

TABLE VII

Ulcerogenic activity of 1-methyl-5-p-methylbenzoylpyrrole-2-acetamido-acetanilides - compounds 1b, 1d, 1f, 1g.

| Compound | Dose mg/kg | Mean number lesions | Mean number severity | Incidence %/10 | Index gastric damage | |
|---|---|---|---|---|---|---|
| Carrier | — | 1 | 1 | 6 | 8 | |
| Tolmetin Na.2H$_2$O | 50 | 2 | 2 | 7 | 11 | +3 |
| Tolmetin Na.2H$_2$O | 100 | 2.5 | 3.5 | 10 | 16 | +8 |
| Tolmetin Na.2H$_2$O | 200 | 3 | 4 | 10 | 17 | +9 |
| 1b | 50 | 1 | 2 | 5 | 8 | +0 |
| " | 100 | 2 | 2 | 7 | 11 | +3 |
| " | 200 | 3 | 3 | 8 | 14 | +6 |
| 1d | 50 | 1 | 1 | 7 | 9 | +1 |
| " | 100 | 1 | 2 | 8 | 11 | +3 |
| " | 200 | 2 | 2 | 8 | 12 | +4 |
| 1f | 50 | 1 | 1 | 6 | 8 | +0 |
| " | 100 | 2 | 3 | 7 | 12 | +4 |
| " | 200 | 3 | 3 | 8 | 14 | +6 |
| 1g | 50 | 1 | 1 | 6 | 8 | +0 |
| " | 100 | 2 | 2 | 7 | 11 | +3 |
| " | 200 | 3 | 2 | 9 | 14 | +6 |

TOXICITY

Acute toxicity of compounds 1b, 1d, 1f, 1g was determined orally and intraperitoneally in two animal species: in male Swiss albino mice 23±2 g in weight and in male Wistar rats 110 g in weight.

Table VIII reports the LD$_{50}$ values (mg/Kg).

TABLE VIII

Acute toxicity of 1-methyl-5-p-methylbenzoylpyrrole-2-acetamidoacetanilides.

| Compound | Animal Species | DL$_{50}$ (mg/kg) os | i.p. |
|---|---|---|---|
| 1b | mouse | >1500 | 1370 |
| " | rat | >1420 | 1195 |
| 1d | mouse | >1500 | 1400 |
| " | rat | 1550 | 1250 |
| 1f | mouse | 1400 | 1000 |
| " | rat | 1300 | 1100 |
| 1g | mouse | >1500 | 1430 |
| " | " | 1470 | 1200 |
| Tolmetin Na.2H$_2$O | mouse | 899 | 550 |
| " | rat | 914 | 612 |

The data reported in Table III–VIII demonstrate the pharmacotherapeutic effect of the 1-methyl-5-p-methylbenzoylpyrrole-2-acetamidoacetanilides at the tested doses and in comparison with the control compounds. The low toxicity of the above compounds means that they have a high therapeutic index: in fact the acute toxicity values are several orders of magnitude greater than those used for pharmacologically active doses. It should also be noted that the ulcerogenic effect is moderate, with regard to both the number of gastric lesions and their severity, in comparison to antiinflammatories in general, which have marked ulcerogenic effects. At the dosages and routes used and indicated in the experiments above, administration to healthy animals led to no mortality over the short or long term, nor gave any apparent signs of toxic effects. The results reported in Table III–VIII demonstrate the therapeutic interest of the pharmaceutical composition according to the invention.

The patients in need of an antiinflammatory, analgesic, antipyretic, and anti platelet aggregant pharmaceutical composition will be orally or parenterally administered a therapeutically effective amount of 1-methyl-5-p-methylbenzoylpyrrole-2-acetamideacetoanilide.

In practice, the compound is orally or parenterally administered in any of the usual pharmaceutical forms which are prepared by conventional procedures well-known to those persons skilled in the pharmaceutical technology. These forms include solid and liquid unit dosage forms such as tablets, capsules, suppositories, solutions, syrups and the like as well as injectable forms, such as sterile solutions for ampoules and phials.

I claim:

1. A compound with the formula

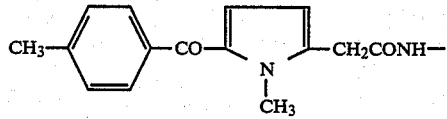

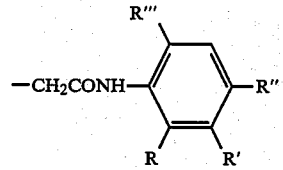

wherein:

R is H, halogen, selected from the group consisting of chlorine, bromine, and fluorine, a straight or branched alkyl chain with 1 to 5 carbon atoms, or alkoxyl with from 1 to 3 carbon atoms;

R' is H, halogen, selected from the group consisting of chlorine, bromine, and fluorine, a straight or branched alkyl chain with 1 to 5 carbon atoms, or alkoxyl with from 1 to 3 carbon atoms or a trifluoromethyl group;

R″ is H or halogen selected from the group consisting of chlorine, bromine and fluorine; and R‴ is H or alkoxy, with from 1 to 3 carbon atoms.

2. A pharmaceutical composition containing as an essential antiinflammatory, analgesic, antipyretic and antiplatelet aggregant active ingredient a therapeutically effective amount of a compound of the formula:

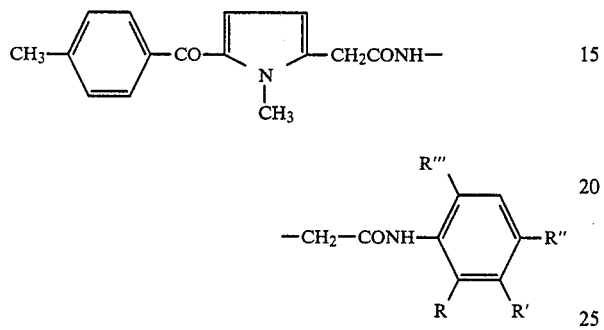

wherein R, R′, R″ and R‴ have the meaning as recited in claim 1 and a pharmaceutically compatible carrier or diluent.

3. A process for the terapeutic treatment of a patient in need of an antiinflammatory, analgesic, antipyretic and antiplatelet aggregant comprising administering a 1-methyl-5-p-methylbenzoylpyrrole-2-acetamidoacetanilide of the formula:

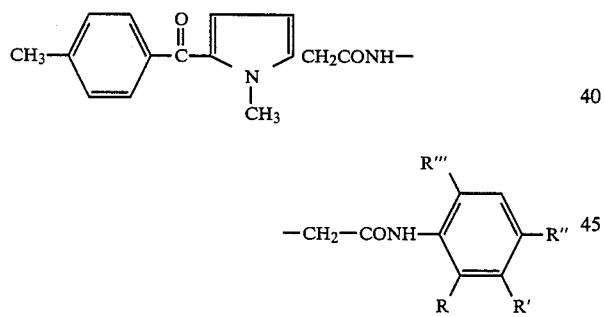

where R, R′, R″ and R‴ have the meaning as recited in claim 1 in an amount effective for such purpose.

4. A compound according to claim 1 wherein R is other than hydrogen.

5. Compound according to claim 1, of formula

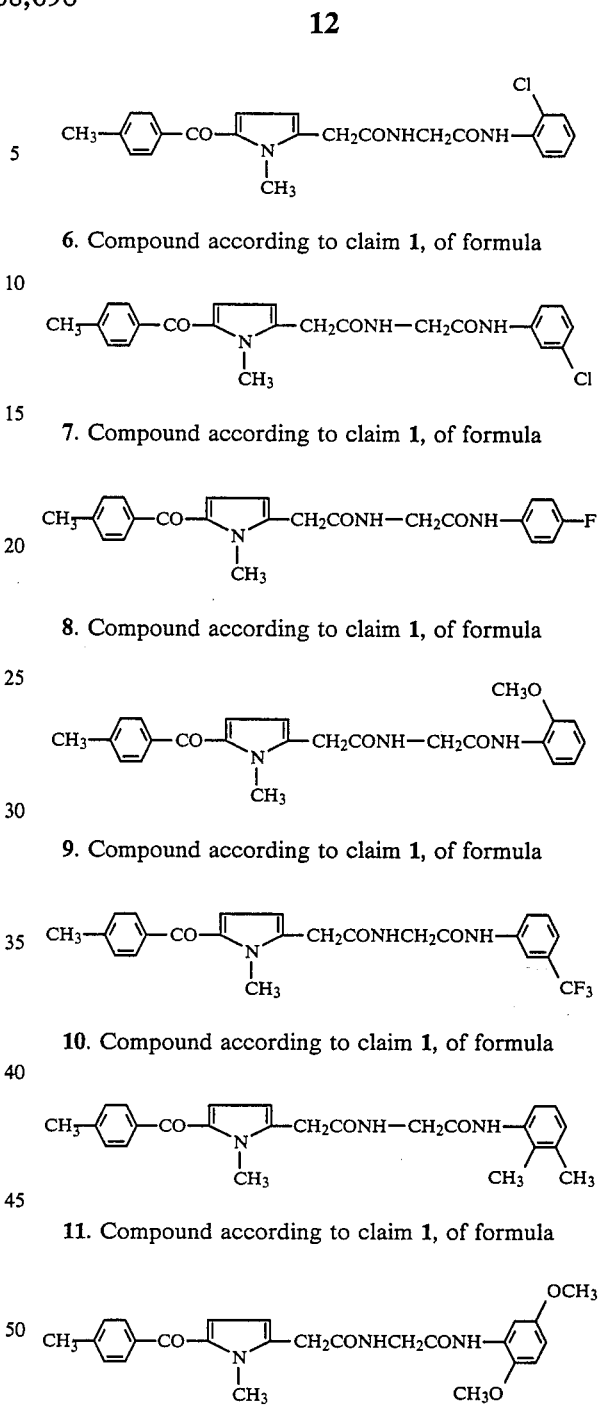

6. Compound according to claim 1, of formula

7. Compound according to claim 1, of formula

8. Compound according to claim 1, of formula

9. Compound according to claim 1, of formula

10. Compound according to claim 1, of formula

11. Compound according to claim 1, of formula

* * * * *